United States Patent
Vidhya et al.

(10) Patent No.: US 9,217,163 B2
(45) Date of Patent: Dec. 22, 2015

(54) PROCESS FOR PRODUCTION AND QUANTITATION OF HIGH YIELD OF BIOBUTANOL

(75) Inventors: Rangaswamy Vidhya, Maharashtra (IN); Isar Jasmine, Maharashtra (IN); Verma Pradeep, Maharashtra (IN)

(73) Assignee: Reliance Life Sciences Pvt. Ltd., Maharashtra (IN)

( * ) Notice: Subject to any disclaimer, the term of this patent is extended or adjusted under 35 U.S.C. 154(b) by 433 days.

(21) Appl. No.: 12/810,270

(22) PCT Filed: Dec. 24, 2008

(86) PCT No.: PCT/IN2008/000864
§ 371 (c)(1),
(2), (4) Date: Jun. 23, 2010

(87) PCT Pub. No.: WO2009/087680
PCT Pub. Date: Jul. 16, 2009

(65) Prior Publication Data
US 2010/0279270 A1 Nov. 4, 2010

(30) Foreign Application Priority Data
Dec. 24, 2007 (IN) .......... 2544/MUM/2007
Jun. 30, 2008 (IN) .......... 1367/MUM/2008

(51) Int. Cl.
*C12Q 1/00* (2006.01)
*C12P 7/16* (2006.01)
*C12P 7/28* (2006.01)
*C12P 1/04* (2006.01)

(52) U.S. Cl.
CPC ... *C12P 7/16* (2013.01); *Y02E 50/10* (2013.01)

(58) Field of Classification Search
None
See application file for complete search history.

(56) References Cited

U.S. PATENT DOCUMENTS

| | | | | |
|---|---|---|---|---|
| 2,089,522 | A * | 8/1937 | Woodruff et al. | 435/150 |
| 2,439,791 | A * | 4/1948 | Beesch | 435/151 |
| 2,902,412 | A * | 9/1959 | Pagano et al. | 536/7.1 |
| 4,443,542 | A * | 4/1984 | Hayashida et al. | 435/160 |
| 4,757,010 | A * | 7/1988 | Hermann et al. | 435/150 |
| 5,063,156 | A * | 11/1991 | Glassner et al. | 435/150 |
| 5,922,921 | A * | 7/1999 | Unruh et al. | 568/882 |
| 6,358,717 | B1 * | 3/2002 | Blaschek et al. | 435/160 |
| 2006/0057118 | A1 * | 3/2006 | Toride et al. | 424/93.4 |
| 2006/0211101 | A1 * | 9/2006 | Chotani et al. | 435/136 |
| 2007/0031953 | A1 * | 2/2007 | Dunson et al. | 435/161 |

(Continued)

OTHER PUBLICATIONS

M. Parekh et al. "Development of a cost-effective glucose-corn steep medium for production of butanol by Clostridium beijerinckii." Journal of Industrial Microbiology and Biotechnology (1998) 21, 187-191.*

(Continued)

*Primary Examiner* — Blaine Lankford
*Assistant Examiner* — Lauren K Van Buren
(74) *Attorney, Agent, or Firm* — Westman, Champlin & Koehler, P.A.

(57) ABSTRACT

The present invention provides a process for production of high yields of butanol by *Clostridium beijerinckii* ATCC 10132. The process can be completed in a shorter span of time, using batch process through manipulation of various process parameters. The process can also be used for biomass based production of butanol. This paves the way for the strategic shift of major chemical industries from the hazardous routes of biofuel production to the biological, environmentally benign one.

4 Claims, 8 Drawing Sheets

Fermentation profile of butanol at 5L scale

Production of butanol in 10L fermentor

(56) References Cited

U.S. PATENT DOCUMENTS

2007/0032549 A1* 2/2007 Grahek et al. .............. 514/548
2007/0275438 A1* 11/2007 David .......................... 435/69.1
2008/0241902 A1* 10/2008 Berry et al. .................. 435/161

OTHER PUBLICATIONS

Madihah et al. "Anaerobic Fermentation fo Gelatinized Sago Starch-Derived Sugars to Acetone-1-Butanol-Ethanol Solvent by Clostridium acetobutylicum." Folia Microbio 46 (3), 197-204 (2001).*
Chen et al. "Acetate enhances solvent production and prevents degeneration in Clostridium beijerinckii BA 101." Appl Microbiol Biotechnol (1999) 52: 170-173.*
Hamilton Company Product Page.*
Parekh et al. "Development of a cost-effective glucose-corn steep medium for production of butanol by Clostridium beijerinckii" Journal of industrial Microbiology and Biotechnology (1998) 21, 187-191.*
Lin et al. "Butanol Production by a Butanol-Tolerant Strain of Clostridium acetobutylicum in Extruded Corn Broth" Applied and Environmental Microbiology , Mar. 1983, p. 966-973.*
*Lin et al. "Butanol Production by a Butanol-Tolerant Strain of Clostridium acetobutylicum in Extruded Corn Broth" Applied and Environmental Microbiology , Mar. 1983, p. 966-973.*
Agarwal, S.K. "Advanced Environmental Biotechnology" published by S.B. Nangia, A. P. H. Publishing Corporation, 2005, p. 10, 94-96.*
Lin et al. "Butanol Production by a Butanol-Tolerant Strain of Clostridium acetobutylicum in Extruded Corn Broth." Applied and Environmental Microbiology, Mar. 1983, p. 966-973.*
Agarwal, S.K. "Advanced Environmental Biotechnology" published by S.B. Nangia, A.P.H. Publishing Corporation, 2005, p. 10, 94-96.*

* cited by examiner

Fig. 1.Effect of different pH on butanol production by *Clostridium beijerinckii* after 84 h of incubation.
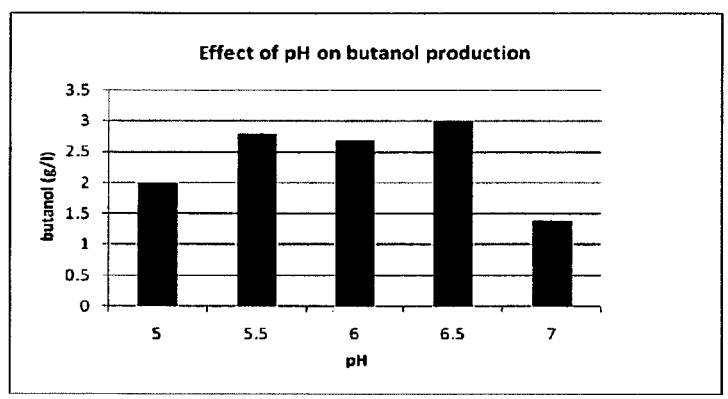
Fig. 2.Effect of different temperatures (°C) on butanol production by *Clostridium beijerinckii* after 84 h of incubation
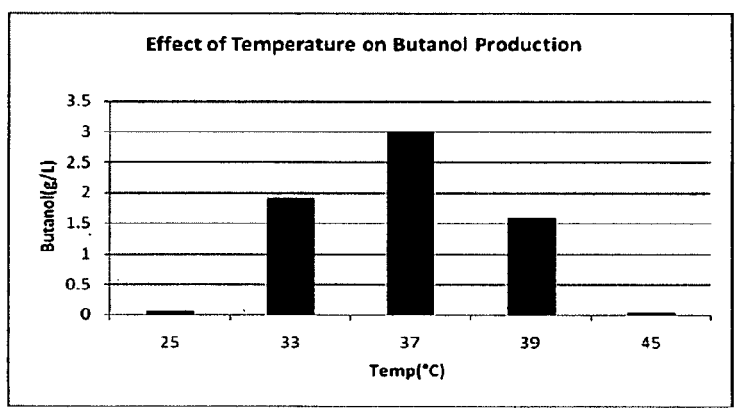

Fig. 3. Effect of different carbon sources (2%) on butanol production.
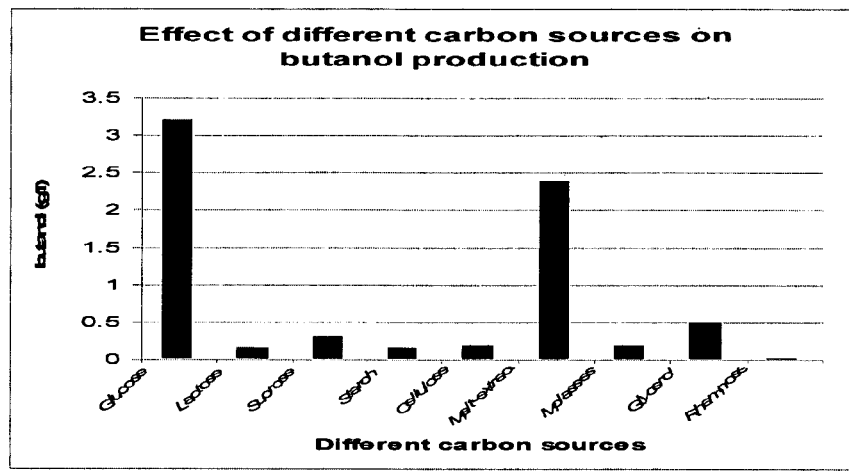
Fig. 4. Effect of different concentrations of glucose on butanol production.
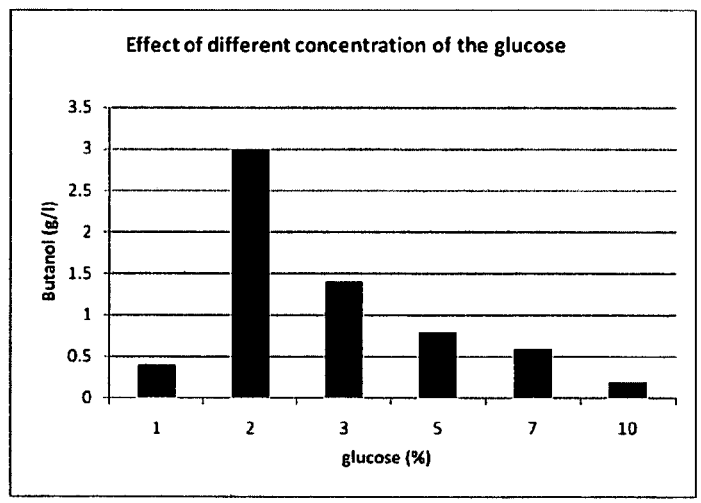

Fig.5: Effect of different concentrations of malt extract on butanol production.
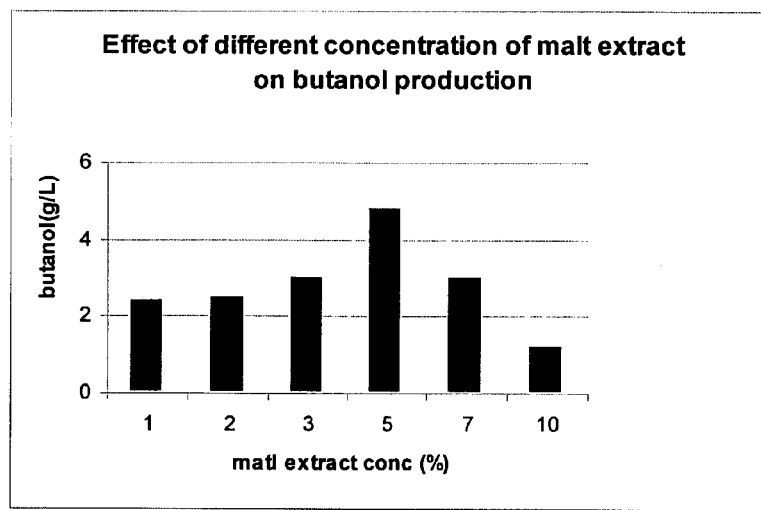
Fig.6: Effect of different nitrogen sources (1.0%) on butanol production
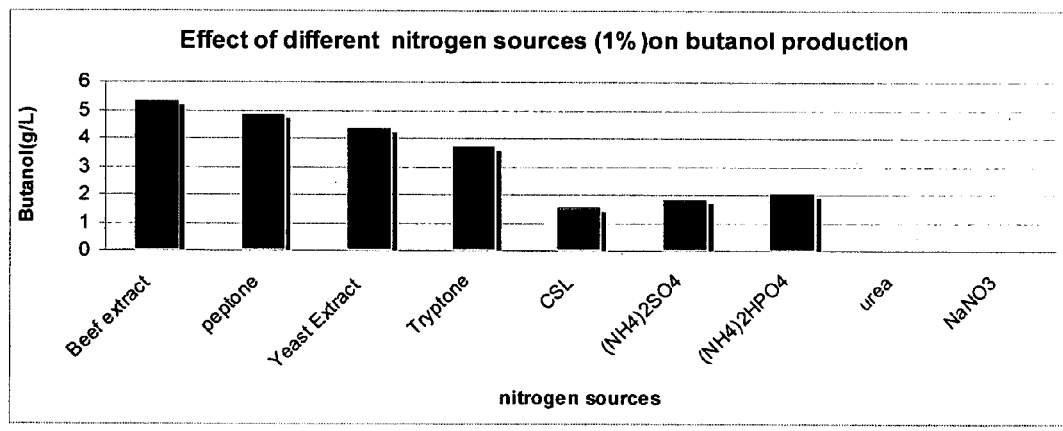

Fig. 7. Effect of different concentrations of beef extract on butanol production
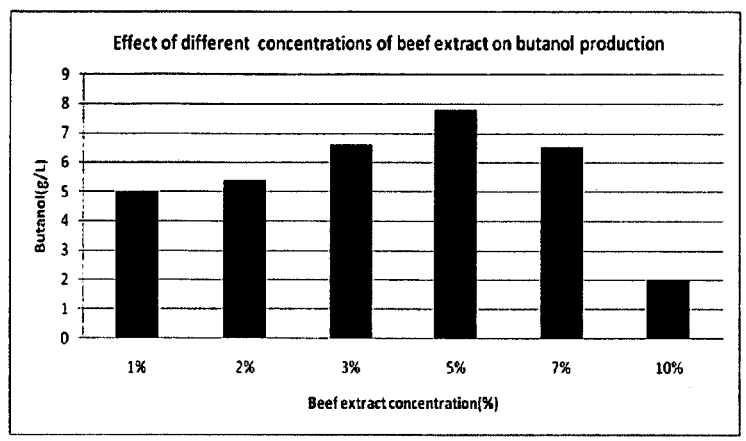
Fig. 8. Effect of different metal ions (0.5%) on butanol production.
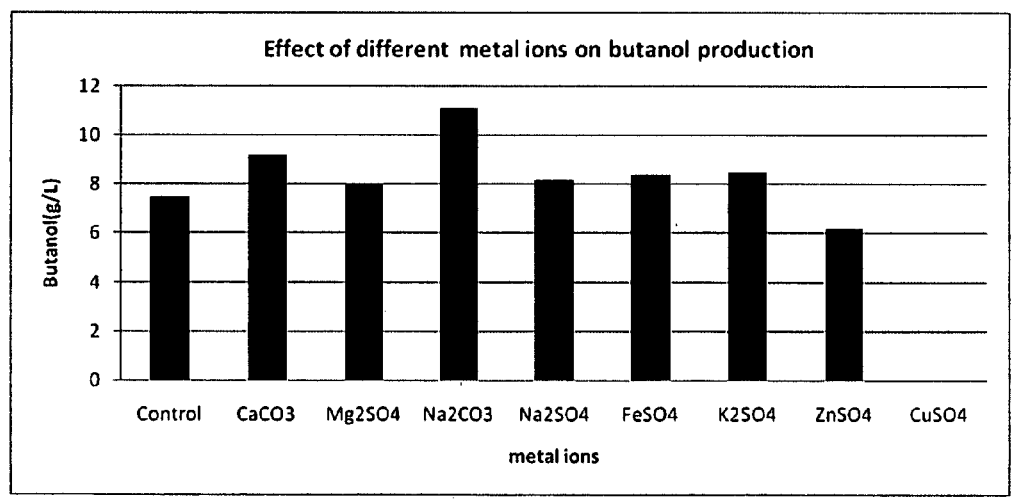

Fig.9. Effect of different concentrations of sodium carbonate on butanol production.
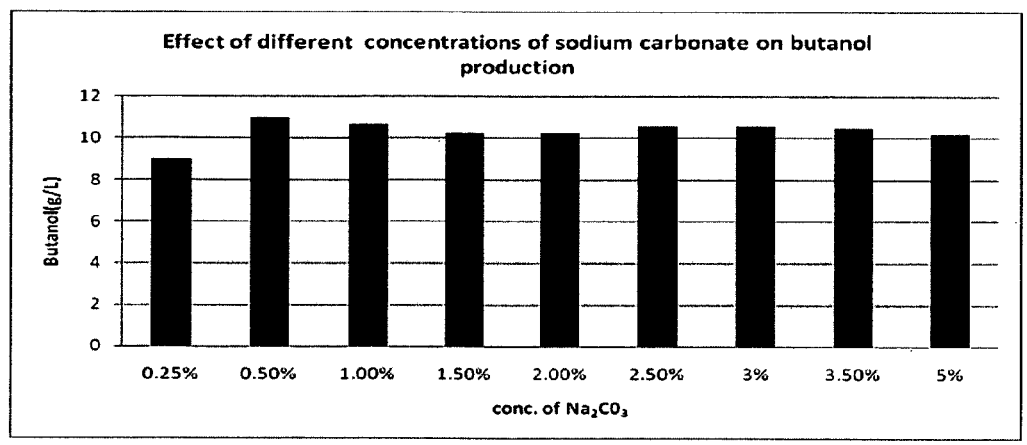
Fig.10. Effect of different inoculum density on butanol production
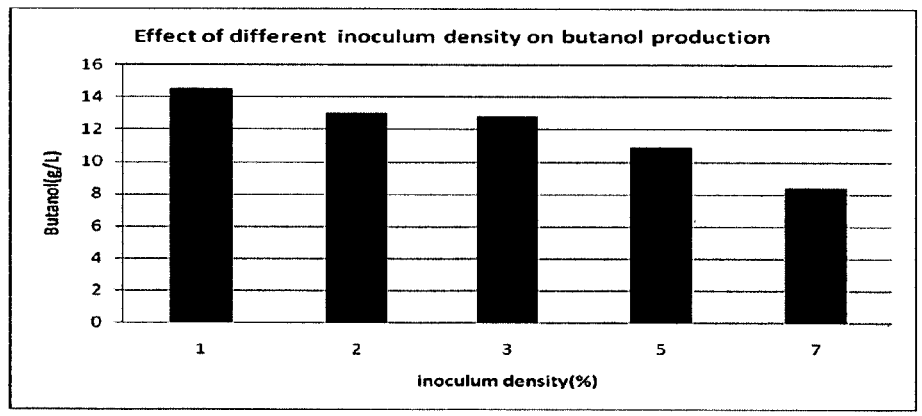

Figure11: Fermentation profile of butanol at 5L scale
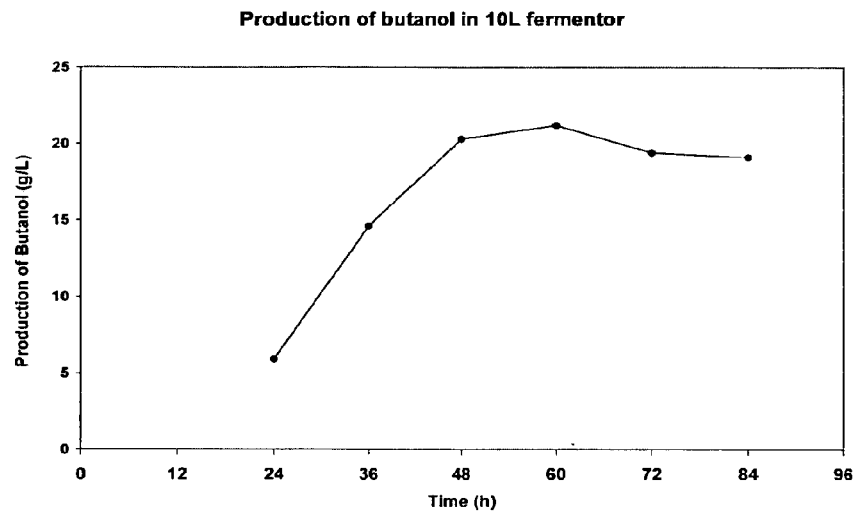
Fig 12: Effect of butanol on growth of C. *beijerinckii* in unoptimised AnS medium
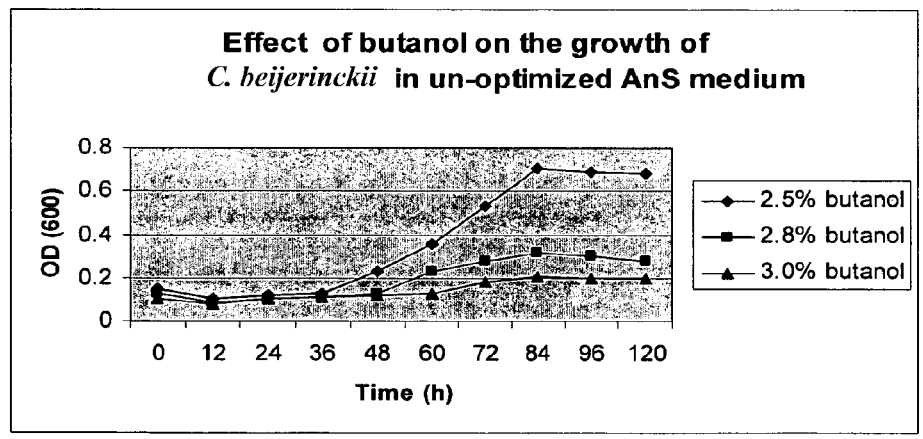

Fig 13: Effect of butanol on growth of *C. beijerinckii* in optimised AnS medium

**Effect of butanol on the growth of *C. beijerinckii* in optimized AnS medium**

[Graph: OD (600) vs Time (h), showing curves for 2.5% butanol, 2.8% butanol, 3.0% butanol, and 3.5% butanol from 0 to 120 hours]

Fig. 14: Western blot analysis for detection of GroEL

[Western blot image with lanes 1, 2, 3 and molecular weight markers at 97, 66, 45]

Lane 1: Un-adapted strain of *Clostridium beijerinckii* ATCC 10132, Lane 2: Solvent-tolerant strain of *Clostridium beijerinckii* ATCC 10132, Lane 3: Rainbow marker Figure 15. HPLC chromatogram of Standard butanol (2.0%)
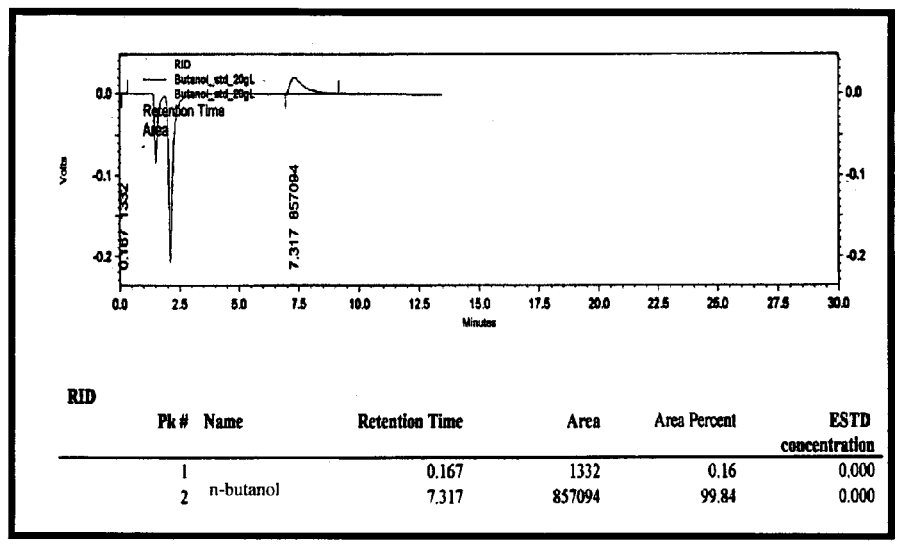
Figure 16. HPLC chromatogram of butanol present in the sample (fermentation broth)
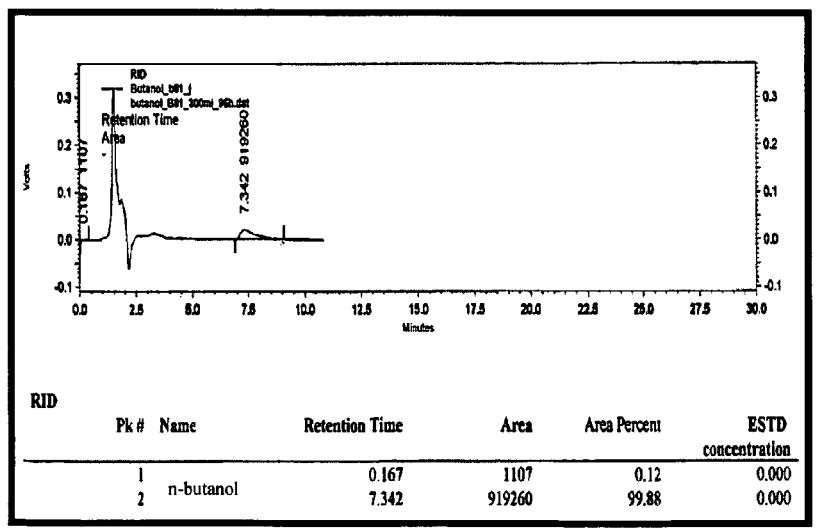

US 9,217,163 B2

PROCESS FOR PRODUCTION AND QUANTITATION OF HIGH YIELD OF BIOBUTANOL

CROSS REFERENCE TO RELATED APPLICATIONS

This application claims benefit of provisional Indian Application No. 2544/MUM/2007, filed Dec. 24, 2007, and provisional Indian Application No. 1367/MUM/2008 filed Jun. 30, 2008 which are hereby incorporated in their entirety by reference.

FIELD OF THE INVENTION

The present invention relates to an improved process of production of high yield of butanol using *Clostridium beijerinckii* ATCC 10132. The present invention in particular reports a strain with enhanced butanol tolerance under the optimized conditions. The present invention also relates to the rapid and efficient method of quantitative estimation of butanol during fermentation process. The present invention in particular relates to the High performance liquid chromatography (HPLC) method for quantitative estimation of butanol produced through anaerobic fermentation carried out using *Clostridium beijerinckii* ATCC 10132.

BACKGROUND OF THE INVENTION

Butanol or butyl alcohol (sometimes also called biobutanol when produced biologically), is a primary alcohol with a 4 carbon structure and the molecular formula of $C_4H_{10}O$. It is primarily used as a solvent, as an intermediate in chemical synthesis, and as a fuel. Today, there is a paramount interest in producing fuels like butanol and ethanol using microorganisms by fermentation focusing on the environmental aspects and renewable nature of this mode of production. Butanol is a superior, fuel and has more calorific value than ethanol (Qureshi and Blaschek, 2000). Butanol has higher energy content than ethanol (110,000 Btu's per gallon for butanol vs. 84,000 Btu per gallon for ethanol). It is six times less "evaporative" than ethanol and 13.5 times less evaporative than gasoline, can be shipped through existing fuel pipelines where ethanol must be transported via rail, barge or truck (Jones and Woods, 1986).

Butanol is an important industrial chemical. Compared to the currently popular fuel additive ethanol, butanol is more miscible with gasoline and diesel fuel, has a lower vapor pressure, and is less miscible with water, qualities that make butanol a superior fuel extender than ethanol. Current butanol prices as a chemical are at $3.75 per gallon, with a worldwide market of 370 million gallons per year. The market demand is expected to increase dramatically if green butanol can be produced economically from low cost biomass. In addition to its usage as fuel, butanol can be used as a solvent for a wide variety of chemical and textile processes, in organic synthesis and as a chemical intermediate. It is also used as paint thinner and a solvent in other coating applications where it is used as a relatively slow evaporating latent solvent in lacquers and ambient-cured enamels. It finds other uses such as a component of hydraulic and brake fluids (Mutschlechner et al., 2000). It is also used as a base for perfumes, but on its own has a highly alcoholic aroma.

Since the 1950s, most butanol in the United States is produced commercially from fossil fuels. The most common process starts with propene, which is run through an hydroformylation reaction to form butanal, which is then reduced with hydrogen to butanol. Butanol is produced by fermentation, from corn, grass, leaves, agricultural waste and other biomass.

Production of industrial butanol and, acetone via fermentation, using *Clostridium acetobutylicum*, started in 1916. Chaim Weizmann, a student of Louis Pasteur, isolated the microbe that made acetone. Up until the 1920s, acetone was the product sought, but for every pound of acetone fermented, two pounds of butanol were formed. A growing automotive paint industry turned the market around, and by 1927 butanol was primary and acetone became the byproduct.

The production of butanol by fermentation declined from the 1940s through the 1950s, mainly because the price of petrochemicals dropped below that of starch and sugar substrates such as corn and molasses. The labor intensive batch fermentation system's overhead combined with the low yields contributed to the situation. Fermentation-derived acetone and butanol production ceased in the late 1950s.

Acetone butanol ethanol (ABE) fermentation by *Clostridium acetobutylicum* is one of the oldest known industrial fermentations. It was ranked second only to ethanol fermentation by yeast in its scale of production, and is one of the largest biotechnological processes ever known. The actual fermentation, however, has been quite complicated and difficult to control. ABE fermentation has declined continuously since the 1950s, and almost all butanol is now produced via petrochemical routes. In a typical ABE fermentation, butyric, propionic, lactic and acetic acids are first produced by *C. acetobutylicum*, the culture pH drops and undergoes a metabolic "butterfly" shift, and butanol, acetone, isopropanol and ethanol are formed. In conventional ABE fermentations, the butanol yield from glucose is low, typically around 15 percent and rarely exceeding 25 percent.

The production of butanol was limited by severe product inhibition. Butanol at a concentration of 1 percent can significantly inhibit cell growth and the fermentation process. Consequently, butanol concentration in conventional ABE fermentations is usually lower than 1.3 percent. The key problem associated with butanol production is butanol toxicity/inhibition of the fermenting microorganism, resulting in low butanol titer in the fermentation broth. (Ezeji et al., 2007). Butanol is highly toxic to biological systems at quite low concentrations of 2% (Jones and Wood, 1986). This toxicity may be because butanol localizes in the plasma membrane and disrupts a number of physiological processes including membrane permeability, solute transport, maintenance of proton motive force, conformation and activity of intrinsic membrane proteins. Efforts are being made to improve the butanol tolerance level in different species of Clostridia with varying degree of success (Evan and Wang, 1988). Recent interest in the production of butanol has lead to re-examination of acetone-butanol-ethanol (ABE) fermentation, including strategies for reducing or eliminating butanol toxicity to the culture.

In the past 20+ years, there have been numerous engineering attempts to improve butanol production in ABE fermentation, including cell recycling and cell immobilization to increase cell density and reactor productivity and using extractive fermentation to minimize product inhibition. Despite many efforts, the best results ever obtained for ABE fermentations to date are still less than 2 percent in butanol concentration, 4.46 g/L/h productivity, and a yield of less than 25 percent from glucose. Optimizing the ABE fermentation process has long been a goal of the industry.

With that in mind, an alternative process was developed using continuous immobilized cultures of *Clostridium tyrobutyricum* and *Clostridium acetobutylicum* to produce an optimal butanol productivity of 4.64 g/L/h and yield of 42 percent. In simple terms, one microbe maximizes the production of hydrogen and butyric acid, while the other converts butyric acid to butanol. Compared to conventional ABE fermentation, this process eliminates acetic, lactic and propionic acids, acetone, isopropanol and ethanol production. The ABE fermentation process only produces hydrogen, butyric acid, butanol and carbon dioxide, and doubles the yield of butanol from a bushel of corn from 1.3 to 2.5 gallons per bushel. The drawbacks associated with such a process are two folds: having to maintain two sets of conditions for the two cultures, maintaining complete anaerobiosis in the immobilized system, dealing with the gases produced during the fermentation and their effect on the maintaining the integrity of the matrix used for immobilization.

In conventional ABE fermentations, the butanol yield, from glucose is low—between 15%-25%—and the butanol concentration in the fermentation is usually lower than 1.3%. (Butanol at a concentration of 1% can significantly inhibit cell growth and the fermentation process.). There have been numerous efforts over the years to improve butanol yield by using a variety of techniques to minimize product inhibition.

In this respect, to develop a process for the maximum production and tolerance of this important fuel by process designing, standardization of media and fermentation conditions, strain improvement is of utmost importance (Agarwal et al., 2005). Physiological and nutritional factors such as initial sugar concentration, complex nitrogen sources, inoculum size, carbonate ion concentrations, pH and temperature of the growth medium are reported to be the most critical factors affecting both cell growth and butanol production (Samuelov et al., 1991; Nghiem et al., 1997; Lee et al., 1999).

U.S. Pat. No. 4,757,010 and European patent application EP 00111683 provides an improved strain of *Clostridium* for increased tolerance to butanol. JP03058782 provides *Clostridium pasteurianum* CA 101 stock (FERM P-10817) as a mutant of genus *Clostridium* bacterium having analog resistance to fermented intermediate of butanol and butanol producibility. U.S. Pat. No. 4,539,293 demonstrates the use of co-culture of microorganisms of the *Clostridium* genus, one favors the production of butyric acid and the other supports the formation of butanol. Japanese patent application JP 63157989 provides production of butanol by culturing a different strain *Clostridium* pasteurianum var. 1-53 (FERM P-9074) in a liquid medium containing a carbon source, a nitrogen source and other inorganic salts at 28-33° C. under slightly acidic pH condition in anaerobic state for 2-4 days.

However the problems associated in these modified strains is that the use of genetically modified strains for fuel production cannot compete with the wild type as one needs to sterilize the feedstock to make sure that there is no competition for the genetically modified organisms. Further genetically modified organisms or various strains are expensive to develop and does not find relevance on high volume products.

Various alternative in situ/online techniques of butanol removal including membrane-based systems such as pervaporation, liquid-liquid extraction, and gas stripping are used.

U.S. Pat. No. 4,777,135 describes a method of producing butanol by fermentation which comprises culturing under anaerobic conditions a butanol-producing microorganisms in a culture medium containing fluorocarbons. This process is not feasible on a commercial scale as the fluorocarbons are environmentally not safe U.S. Pat. No. 4,605,620 provides a process for butanol by using a medium containing carbohydrate and phosphate, wherein the experiments were performed with a total phosphate content of 1.0-0.4 mmoles. This process poses a restriction wherein the phosphate limiting medium is required.

U.S. Pat. No. 4,560,658 provides a process for the production of butanol by fermentation of carbon containing compounds with *Clostridium acetobutylicum* wherein the fermentation is conducted in an aqueous medium containing a sufficient concentration of dissolved carbon monoxide. However the use of carbon monoxide make the process environmentally unsound.

U.S. Pat. No. 4,520,104 provides a process for the continuous production of butanol by fermentation of carbohydrates with *C. acetobutylicum*. This process combines continuous inoculum production at a high dilution rate and cycling the fermentation broth through material which adsorbs butanol whereby a vigorous cell population is maintained in the fermentation reactor for extended periods of time. The process is devised to remove the butanol produced in the broth so as to prevent its toxicity on the cells Japanese patent JP 62278989 provides a fermentation process for the production of acetone and butanol, by keeping a butanol-producing strain in resting state, adding a carbon source to the cell to effect the production of acetone and butanol in a short time, recovering and concentrating the butanol-producing strain, subjecting to the heat shock and adding to a fermentation tank Heat shock is required in the process.—to activate the spores of *Clostridium* and is pretty routine.

Japanese patent application provides an anaerobic cellulolytic germ, e.g. *Clostridium cellobioparum* ATCC15832 or *Ruminococcus albus* ATCC27211, and *Clostridium saccharoperbutylacetonicum* are inoculated into a culture medium containing a material containing cellulose, e.g. wood, waste paper or pulp, as a main carbon source, and cultivated at 25-45° C. and 4-9 pH under anaerobic conditions for about 2-20 days to collect the aimed compound, containing oxygen, and consisting essentially of butanol from the resultant culture. This process is time consuming and takes about 20 days for completion, hence not feasible on a large scale.

Japanese patent 63269988 discloses butanol fermentation wherein yeast is subjected to autodigestion in a fermentation tank and proliferated prior to the inoculation of butanol-producing strain. The space in the fermentation tank becomes anaerobic and the temperature increases by the proliferation of yeast to perform butanol fermentation. An inefficient autodigestion would lead to contamination of the broth by the yeast US20050233031 provides a process for producing butanol which includes treating plant derived material to provide an aqueous liquor containing sugars in a fermentation process to produce a fermentation product. The process involves several steps and therefore cumbersome and tedious.

Japanese Patent JP 200535328801 provides a method for producing butanol in which a culture solution is prepared by using a formulation of the food residue with the Japanese distilled spirit lees and water and butanol fermentation is carried out in the culture solution. The use of Japanese distilled spirit is limited to the production experiments performed in Japan.

French patent FR2550222 provides a two stage process wherein a first stage of seeding with *Clostridium acetobutylicum* and a second stage of seeding with a yeast which produces ethanol, the second stage being commenced when the pH of the fermentation medium of the first stage has reached a minimum value. The invention applies in particular to the production of butanol, acetone and ethanol from sugarbeet and Jerusalem artichoke juices. The process requires pretreatment which makes it cumbersome.

Although, there are reports where microbes have been exploited for the production of butanol by fermentation, an economically viable biosynthetic process for butanol production is yet to be developed (Jesse et al., 2002).

Mustafa et al provided mid-infrared spectroscopy coupled to sequential injection analysis for the on-line monitoring of the acetone—butanol fermentation process. This involves the use of highly sophisticated instruments/skills which are not available in many laboratories. (Mustafa K. et al., Spectroscopy Letters, 38, 677-702 (2005))

Gas chromatography and gateway sensors for on-line state estimation of complex fermentations (butanol-acetone fermentation) showed a fermentation system that has been designed to demonstrate the use of gas chromatography (GC) for on-line monitoring of the butanol-acetone and other complex saccharolytic fermentations. (McLaughlin J K, Meyer C L, Papoutsakis E T. (1985) Biotechnology and Bioengineering Volume 27, Issue 8, Pages 1246-1257). However, parameters include glucose concentration and gas composition, as well as a number of unobservable parameters (such as $Y_{ATP}$, excess ATP, and NAD reduced by FdH2), which characterize the state of the fermentation. Hence this method is very tedious requiring numerous parameters to be monitored.

U.S. Pat. Nos. 4,521,516, 4,520,104, 4,560,658, 4,649,112 disclose methods of HPLC determination of butanol wherein the components were analyzed chromatographically by elution with 0.006N $H_2SO_4$ from a cation-exchange resin in the hydrogen form. The eluted components were detected by means of a differential refractometer, plotted on a recorder and quantitated using an electronic integrator. The area under the curve which represents the concentration of each component is reported as a percentage of the total area. The general procedure followed was that given in "Analysis of Carbohydrate Mixtures by Liquid Chromatography", Am. Soc. Brew. Chem. Proc., 1973, pp. 43-46. The separations were made on a 1-foot HPX-87 column in the hydrogen form, available from Bio-Rad Laboratories, Richmond, Calif. The Residual total carbohydrate (RTC) in the fermentation medium was measured by the phenol/sulfuric acid method which has been described in detail by Dubois, et al, "Colorimetric Method Determination of Sugars and Related Substances", Anal. Chem., 28, 350-356 (1956)

Hence these above cited methods where generally GC is used for the estimation of butanol (Bryant and Blaschek, 1988). requires extraction or derivatization of butanol in hexane or other solvents before analyzing the samples. This makes the process tedious and there may be some losses during the extraction or derivatization steps. A couple of HPLC methods have been reported (Ehrlich et al., 1981) for the estimation of butanol. But even in these methods, the run time is too long (30-50 min) to detect the butanol. Hence such a method can not be used for analyzing large number of samples.

OBJECTS OF THE INVENTION

As there is a need for a process which yields enhanced production of butanol, the present invention provides an ideal culture condition for the wild strain of *Clostridium* which will result in enhanced butanol tolerance and subsequently the in yields of butanol.

As there is a need for developing a method for analysis of butanol during the fermentation, the present invention provides an efficient and robust method for butanol analysis by HPLC encompassing the drawbacks associated with the known methods for butanol analysis. The present invention provides a simple and cost effective HPLC method wherein the quantitative estimation of butanol can be achieved without the need of extraction and within a short retention time. The present invention has successfully improved the rate of analysis thus efficiently monitoring the fermentation process.

It is the object of the present invention to provide an improved process for the production of high yield butanol using *Clostridium beijerinckii* ATCC 10132 without any change in the strain of the microorganism.

It is the object of the present invention to provide optimal fermentation conditions for enhanced production of butanol, using *Clostridium beijerinckii* ATCC 10132.

It is the object of the present invention to provide a process with optimal fermentation conditions, which will result in increased butanol tolerance of the microorganism.

It is the object of the present invention to provide a culture condition for high yields of butanol fermentation.

It is the object of the present invention to provide a process for increased yields of butanol in a single batch fermentation conditions.

It is the object of the present invention to provide a process for biobutanol using various biomass.

It is the object of the present invention to provide a cost effective and industrially scalable process for butanol.

The present invention aims to provide a simple, fast and reliable HPLC method of quantitative estimation of butanol It is the aim of the present invention to provide a cost effective HPLC method for determination of butanol during the fermentation process.

It is the aim of the present invention to detect butanol in the fermentation broth which can be applied for analysis of large number of samples on a routine basis.

SUMMARY OF THE INVENTION

The present invention relates to an efficient process for the production of high yield of butanol using *Clostridium beijerinckii* ATCC 10132, without any change in the strain of the microorganism resulting in enhanced production of butanol. The present invention in particular aims at providing optimal culture conditions that would result in increased butanol tolerance of the microorganism. The present invention further aims at providing a cost effective and industrially scalable process for the production of butanol.

One problem associated with the ABE fermentation by *C. acetobutylicum* and *C. beijerinckii* is butanol toxicity to the culture. This toxicity requires continuous removal of the toxic products during the process for maximum production of solvents. A novel aspect of the present invention is the production of high yields of butanol (upto 20 g/L) in a single batch process, without stripping the butanol produced. The process does not involve any fed-batch step which would involve extra step of addition of nutrients. Neither is any solvent-stripping required for reaching this high yield. Unlike many reported processes which employ continuous mode of fermentation thereby increasing the chances of contamination, the present process can be completed in a single batch mode. Careful optimization of the medium and acclimatization has resulted in a strain that is capable of producing and tolerating such high yields of butanol in the broth. Thus, all these parameters make the process of the present invention more cost-effective. Further the inventors have also been able to successfully demonstrate the process at 5 L scale.

In one aspect the present invention provides a process with increased butanol tolerance without the need of modifying the strain. In one preferred aspect the present invention provides tolerance to about 2.5% butanol concentration under optimized medium conditions directed to a process for providing the increased yield of butanol as provided in this invention. The most probable reason for its high tolerance to butanol may be that the process optimization has resulted in the final set of physio-chemical conditions under which the above mentioned limitations are alleviated. For example the redox potential, osmolarity, electron flow may have been altered under the optimized conditions. Certain set of enzymes required for butanol tolerance and production may have been activated or induced under the optimized conditions. The culture may have adapted during the course of the optimization process to high butanol level.

In one aspect the present invention provides a process with increased yields of butanol. In one aspect the present invention reports up to a 9-fold increase in butanol production in 500 ml anaerobic bottles containing 300 ml of the optimized Anaerobic Sugar (AnS) medium as against the initial un-optimized AT medium (50 ml).

In one aspect the present invention provides a process for evaluation of the biobutanol using various biomass. In one preferred aspect the seeds from Jatropha and banana stems were used. The yield of biobutanol using the seeds and stems pretreated under different conditions such as alkaline, acidic and microwave digestion was also studied.

In one aspect the present invention provides a process which can be scaled up on a large scale.

The following drawings form part of the present specification and are included to further demonstrate certain aspects of the present disclosure, the inventions of which can be better understood by reference to one or more of these drawings in combination with the detailed description of specific embodiments presented herein.

The present disclosure provides a simple, efficient and reproducible method for quantitative estimation of butanol employing HPLC. The conditions for HPLC have been developed for obtaining a retention time less than that of the conventional methods. This helps in reducing the time for estimation of butanol and aids in effectively monitoring the progress of the fermentation also. The HPLC method developed can also be used for routine analysis of the large number of samples. The present invention in particular provides a HPLC method of determination of butanol during its fermentation process.

In one embodiment the present invention utilizes a column selected from a series of ion exchange columns.

In one embodiment the present invention utilizes detector system which measures a Refractive Index.

The present invention relates to the determination of butanol during the fermentation process by a simple HPLC method. The method is simple in that the analysis does not require any extraction of the product and the sample required for injection is the supernatant of the fermentation culture medium.

The analysis of the sample involves detection of butanol which is linear up to 2.5%. The process can be used for both the quantitative and qualitative estimation of butanol. The method in particular is used for the detection of butanol in the fermentation broth which can be applied for analysis of large number of samples on a routine basis.

BRIEF DESCRIPTION OF THE DRAWINGS

FIG. 1 shows the effect of different pH on butanol production by *Clostridium beijerinckii* ATCC 10132 after 84 h of incubation.

It was observed that though butanol was produced in the pH range 5.0 to 7.0 the optimal pH for production is 6.5, yielding 3.2 g/l of butanol in 84 h.

FIG. 2 shows the effect of different temperatures (.degree. C.) on butanol production by *Clostridium beijerinckii* ATCC 10132 after 84 h of incubation.

Results on the effect of different temperatures (25, 33, 37, 39 & 45° C.) showed that 3.0 g/l of butanol was produced at 37±2° C. in 84 h. However at 25 and 55° C., no significant butanol production was observed FIG. 3 shows the effect of different carbon sources (2%) on butanol production.

While studying the effect of nutritional factors, it was observed that none of the carbon sources tested supported as much butanol (3.2 gL$^{-1}$) as was produced in the control viz. in glucose. This was followed by malt extract that supported 2.4 gL$^{-1}$ of butanol in 84 h FIG. 4 shows the effect of different concentrations of glucose on butanol production.

It was found that 2.0% w/v glucose concentration supports maximum yield of 3.2 gL$^{-1}$ of butanol FIG. 5 shows the effect of different concentrations of malt extract on butanol production.

Concentration of malt extract, the second best sugar source, was varied in the medium (1.0-10%). 4.82 gL$^{-1}$ of butanol was produced when 5% malt extract was added along with 2% glucose in the AnS medium FIG. 6 shows the effect of different nitrogen sources (1.0%) on butanol production Beef extract was found to be the best nitrogen source among various nitrogen sources tested resulting in the production of 5.2 gL$^{-1}$ of butanol FIG. 7 shows the effect of different concentrations of beef extract on butanol production Optimization of concentration showed that 5.0% w/v' of beef extract is optimum for butanol production (7.8 gL$^{-1}$)

FIG. 8 shows the effect of different metal ions (0.5%) on butanol production.

A significant increase in butanol production (11.1 gL$^{-1}$) was achieved when the medium optimized so far was supplemented with Na$_2$CO$_3$ at 0.5%. This is followed by calcium ions that resulted in the production of 9.2 μL$^{-1}$ of butanol. Metal ion like Cu did not support any amount of butanol production FIG. 9 shows the effect of different concentrations of sodium carbonate on butanol production.

It was observed that 0.5% w/v of Na$_2$CO$_3$ is optimal for butanol production (11.0 gL$^{-1}$).

FIG. 10 shows the effect of inoculum density on butanol production

It was observed that, 14.5 gL$^{-1}$ of butanol was produced at the inoculum density of 1%. However, with increase in the inoculum density beyond 2%, the production of butanol declined.

FIG. 11 shows the fermentation profile of butanol at 5 L scale

The fermentation profile at 5 L scale indicates that the production of butanol is much faster at higher scale with the yield reaching 20 g/L in 48 h and reaching a plateau thereafter.

FIG. 12 shows the effect of butanol on the growth of *Clostridium beijerinckii* ATCC 10132 in un-optimized AnS medium.

FIG. 13 shows the effect of butanol on the growth of *Clostridium beijerinckii* ATCC 10132 in optimized AnS medium.

FIG. 14 shows the results of a Western blot analysis for detection of GroEL.

FIG. 15 shows HPLC chromatogram of standard butanol.

FIG. 16 shows HPLC chromatogram of butanol present in the sample (fermentation broth).

DETAILED DESCRIPTION OF THE INVENTION

Definitions

The term Butanol or biobutanol as used herein refers to n-butanol.

The term butanol tolerance as used herein refers to the ability of the bacterium to survive and grow in the presence of ≥1.3% butanol in the medium The term *Clostridium beijerinckii* ATCC 10132 refers to the bacteria that has the ability to produce butanol along with acetone and ethanol in an anaerobic fermentation.

The term yield as used herein refers to amount of butanol produced in the fermentation broth in g/L.

The term HPLC as used herein refers to high pressure liquid chromatography.

The term "impurities" as used herein refers to the byproducts like acetone, ethanol, etc. produced during the process.

Methods for Butanol Production As pH is one of the important factors that affect both growth and growth-associated production of molecules, butanol production was examined at different pH. The optimal pH for butanol production by *Clostridium beijerinckii* ATCC 10132 in the present invention was 6.5. This is in accordance to the findings of Robson and Jones (1982), who reported that *C. acetobutylicum* P262 showed good levels of solvent production within the pH range of 5.0-6.5. Similarly, Bielbl (1999) reported that *Clostridium beijerinkii* NCIMB 8052 showed much better growth and solvent production at pH 5.5 than at pH 5.0 or below.

The present invention has found that temperatures of 37±2° C. is the optimal temperature for butanol production from *Clostridium beijerinckii* ATCC 10132. This is in contrast to the earlier findings of McCutchan and Hickey (1954) who reported a decrease (upto 23%) in the solvent production by *Clostridium* sp. at 37° C. as against the fairly constant yields of 31% at 30 and 33° C.

The effect of carbon sources on butanol production by *Clostridium beijerinckii* ATCC 10132, was studied and it was observed that glucose supported the highest butanol production. This was followed by malt extract, the second best carbon source. However, carbon sources like glycerol and sucrose supported a moderate amount of butanol. Sugars like rhamnose were not at all utilized by the strain. The most probable reason could be that the strain was unable to transport 2-deoxy glucose sugar.

The study on the concentration of the sugars revealed that 2% glucose, supported 3.2 $gL^{-1}$ of butanol. Similar has been reported by Biebl (1.999) who observed maximum butanol production by *C. acetobutylicum* ATCC 824 in the medium containing 2.8% of glucose. However, in most of the studies, 6-7% has been found to be the optimum glucose concentration for butanol production. In this direction Parekh et al. (1998) reported that 6.0% glucose in the medium yielded 10.0 g/l of butanol from *C. beijerinkii* 8052 strain after 90 h of incubation.

Subsequently, when malt extract levels were varied in the medium in the range (1.0-10% w/v) while keeping the concentration of glucose constant (at 2%), 4.8 $gL^{-1}$ of butanol was produced at 5% malt extract. Similarly, the effect of nutrition limitation on the onset and maintenance of solvent production has been investigated by a number of other workers. For example, Long et al., (1984) reported that in the batch fermentation using *Clostridium acetobutylicum* P262, only acids were produced when the concentration of the carbon sources was limited.

On supplementation of the medium with 5% beef extract, a maximum of 5.3 $gL^{-1}$ of n-butanol was produced as against the control (1% peptone) wherein 4.8 $gL^{-1}$ of butanol production was observed. The most probable reason for beef extract being good source of nitrogen is because it not only provides nitrogen but also vitamins, and other nutrients which are essential for the growth of the microorganism Metal ions are known to play an important role in maintaining cellular metabolism and enzyme activities (Isar et al., 2006). A significant increase in butanol production was achieved when the medium optimized so far was supplemented with $Na_2CO_3$. The reason could be that $Na^+$ is a cofactor for most of the enzymes involved in the anaerobic pathway. Strobel et al. (1991) and Lee et al., (2000) reported that sodium ions are an important factor for the nutrient uptake. These ions are involved in the formation of transmembrane pH gradient, cell motility and intracellular pH regulation. Amongst different salts of sodium ion investigated, it was found that carbonate and bicarbonate were the most effective radicals for the production resulting in approximately 11.2 $\mu L^{-1}$ of butanol.

Change in the inoculum density from 1-2% did not significantly influence butanol production. However, an increase in inoculum density beyond 2% results in a decline in the production of the solvent. The most probable reason could be that as the inoculum size is increased beyond 2%, there is nutrition limitation.

The present invention provides the effect of different physiological and nutritional parameters on butanol production by *Clostridium beijerinckii* ATCC 10132. This strain initially produced 0.2 $gL^{-1}$ of butanol in 84 h in Alternate Thioglycollate medium.

However, when process optimization was employed, 20.0 $gL^{-1}$ of butanol was produced in 300 ml of the optimized AnS medium consisting of Glucose (2%), Beef extract (5%), Malt extract (5%) Yeast extract (0.5%), $K_2HPO_4$ (0.3%), $Na_2CO_3$ (0.6%), $(NH_4)_2SO_4$ (0.1%), $CaCl_2.2H_2O$ (0.02%), $MgCl_2.7H_2O$ (0.02%), $Na_2S(0.002\%)$, at pH 6.5, 37° C., under static conditions (with gentle intermittent manual shaking) in 96 h. Interestingly, it was also observed that the strain is tolerant to 2.5% butanol under optimized medium and conditions.

The verification of the process in 300 ml medium clearly indicated that the process can be scaled up to higher size and about 20 $gL^{-1}$ of butanol could be produced. The most probable reason for this increase in the yield could be the availability of more head space in bigger size bottles as against the smaller bottles.

The *Clostridium* strain used in the present invention has shown tolerance to 2.5% butanol. The most probable reason for its high tolerance to butanol may be that the process optimization has resulted in the final set of physio-chemical conditions under which the above mentioned limitations are overcome. For example, the redox opotential, osmolarity, electron flow may have been altered under the optimized conditions. Certain set of enzymes required for butanol tolerance and production may have been activated or induced under the optimized conditions. The culture may have adapted during the course of study (optimization process). Since the actual tolerance level of this strain has never been reported earlier, it may also be the intrinsic un-exploited property of the strain. In several instances, a strain normally not reported to produce a biomolecule starts making it in significant amounts after process optimization (Isar et al., 2006).

Further studies on utilization of various biomass for butanol production using the conditions described above was performed. In particular, the biomass studied was jatropha seed cake and banana stem. Various pretreatments were given to the biomass prior to its use for the production of butanol.

These pretreatments make the sugars from the biomass available for fermentation. The pretreatments include subjecting to fungal degradation, acid treatment, alkali treatment or microwave digestion.

Jatropha seed cake was incubated with fungal culture *Pleurotus ostreatus* at 23° C. for a month and the biomass was extracted with a buffer. After extraction, the biomass was used as a supplement at different concentrations (1, 3, 5 and 10%) in Anaerobic sugar medium having 0.5% calcium carbonate. A yield of 8.4 g/l of butanol was obtained after 48h using 3% of the fungal pretreated jatropha seed cake.

In addition to this, when 1% soybean meal was added in AnS medium supplemented with 0.5% calcium carbonate and 4% of Beef extract a maximum yield of 10.5 g/L of butanol after 96 h.

Experiments were also done on Banana stem and jatropha seed pretreated with sodium hydroxide. The alkali treated biomass was supplemented at various concentrations in AnS medium having 0.5% calcium carbonate. At 1% supplementation, a yield of 8.1 g/L butanol was obtained in AnS medium containing predigested banana stem as against 5.0 g/L butanol with predigested jatropha seed cake.

With microwave digested biomass supplementation, a yield of 6.9 g/l of butanol was obtained after 84 h when 2% microwave treated banana stem was added to AnS medium having 0.5% calcium carbonate. With 1% microwave digested jatropha seed cake supplementation, 7.0 g/l of butanol was obtained after 84 h.

Supplementation with 0.1 N Sulphuric acid treated biomass in AnS medium having 0.5% calcium carbonate resulted in a yield of 5.0 g/l of butanol after 84 h for 1% banana stem and a yield of 4.0 g/l of butanol after 84 h for 1% jatropha seed cake.

Quantitation of butanol production by HPLC The present invention relates to the use of HPLC method for the quantitative estimation of butanol, which is less time consuming, cost effective having increased industrial viability. as the run time indicating the presence of n-butanol is much less as less as 7.3 min as compared to (30-50 min) of the methods available in public domain. The factors that are responsible to reduce the run time is the optimal combination of the mobile phase solvents acetonitrile and 0.5 mM $H_2SO_4$ (1:9). The flow rate has also been optimized to 1.5 ml/min. The method in particular is used for the detection of butanol in the fermentation broth which can be applied for analysis of large number of samples on a routine basis.

The present invention relates to development of a quick and efficient High Performance Liquid Chromatographic (HPLC) method for the estimation of butanol produced through anaerobic fermentation carried out using *Clostridium beijerinckii* ATCC 10132. Here, a PRP 300X (Hamilton) column is used for the estimation of butanol on a HPLC system where acetonitrile and 0.5 mM $H_2SO_4$ (1:9) is used as the mobile phase, at a flow rate of 1.5 ml/min at 37° C. RI is used as the detector.

As stated above the previous reports on the use of HPLC, the run time for estimation of butanol is as high as 30-50 min, making it difficult to analyse large number of samples. Similarly, the GC method reported for the estimation of butanol requires extraction or derivatization of the sample, which can lead to handling loss.

To date there has been no publication on the reports on the use of HPLC, showing a reduced run time below 30 min for estimation of butanol. The inventors of the present invention have developed a process that provides the run time which as low as 7.6 min to detect a sample and does not require any extraction procedures. The importance of the invention is that it takes very short time (7.3 min) to efficiently detect the butanol present in the fermentation broth. Hence a huge number of samples can be analysed on routine basis in a very short time.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Organism and Growth Conditions

*Clostridium beijerinckii* ATCC 10132 was grown in 125 ml anaerobic bottles containing 50 ml of the Anaerobic Sugar (AnS) medium with the composition (gL$^{-1}$): Glucose (20.0); Peptone (10.0); Yeast Extract (5.0); $K_2HPO_4$ (3.0); NaCl (1.0); $(NH_4)_2SO_4$ (1.0); $CaCl_2 2H_2O$ (0.2); $MgCl_2 6H_2O$ (0.2); and $Na_2CO_3$ (1.0), pH 6.5.

The medium was sterilized (15 min, at 121° C.) in glass bottles sealed with butyl rubber bungs. The headspace was filled with by $N_2$, and $Na_2S.9H_2O$ (0.02%) was added to remove traces of dissolved oxygen (Samuelov et al., 1991; Lee et al., 2000). The reduced medium was inoculated with 2% seed inoculum and incubated at 37±1° C. for 96 h with intermittent gentle shaking.

Example 2

Methods for Estimation of Butanol

After the desired incubation period, the culture was withdrawn from the sealed vials using sterile disposable syringes and was centrifuged at 8000×g in a Eppendorf centrifuge (model no 54151) for 10 min. Supernatant was filtered through 0.45□ filter. The sample (20 µl) were analysed by HPLC, (Ehrlich et al., 1981) on a PRP 300X' column (Hamilton) using acetonitrile and 0.5 mM $H_2SO_4$ (9:1) as the mobile phase, at a flow rate of 1.5 ml/min at 37° C. Butanol was detected using a RI detector.

Example 3

Process in Batch Fermentation

Various media tested for butanol production were Anaerobic sugar (AnS) medium, (Isar et al., 2006); Reinforced Clostridial (RC) medium, (Lin and Blaschek, 1983); Soluble Starch Medium (SSM), (Moreira et al., 1981); Alternate Thioglycollate (AT) media, (Lin and Blaschek, 1983); Potato Starch media (PSM), (Fouad et al., 1976). Amongst the media tested, AnS medium was the best yielding 3.2 g/l of butanol (Table 1). Butanol production was optimized in the AnS medium where the effects of different physiological and nutritional parameters were studied.

TABLE 1

Butanol production (g/l) in different media

| Time (h) | AnS | RC | AT | SSM | PSM |
|---|---|---|---|---|---|
| 12 | 0.31 | — | — | — | — |
| 24 | 0.43 | — | 0.02 | — | — |
| 36 | 0.6 | 0.01 | 0.03 | — | — |
| 48 | 1.2 | 0.02 | 0.09 | 0.01 | 0.09 |
| 60 | 2.1 | 0.05 | 0.1 | 0.04 | 0.09 |
| 72 | 2.2 | 0.10 | 0.2 | 0.07 | 0.10 |
| 84 | 3.2 | 0.13 | 0.2 | 0.09 | 0.11 |
| 96 | 3.0 | 0.11 | 0.1 | 0.08 | 0.09 |

Subsequently, the effect of pH (5-7) and temperature (25-45° C.) was studied in the selected medium for butanol production. It was observed that the optimal pH for production is 6.5, yielding 3.2 g/l of butanol in 84 h (FIG. 1). Results on the effect of different temperatures (25, 33, 37, 39 & 45° C.) showed that 3.0 g/l of butanol was produced at 37±2° C. in 84 h (FIG. 2).

Optimization of the nutritional parameters including carbon source, nitrogen source, metal ions required for maximum production of butanol was carried out. Various carbon sources employed include glucose, fructose, sucrose lactose, malt extract and glycerol at a concentration of 2.0% w/v in the medium. None of the carbon sources supported as much butanol production (3.2 gL$^{-1}$) as glucose in 84 h (FIG. 3). Further, 2.0% w/v glucose gives the highest yield i.e. 3.2 gL$^{-1}$ of butanol (FIG. 4). Approximately, 4.82 gL$^{-1}$ of butanol was produced when 5% malt extract was added along with 2% glucose in the AnS medium (FIG. 5).

For nitrogen source optimisation, peptone (1% w/v) in the medium was replaced by different inorganic (ammonium hydrogen phosphate, ammonium chloride, sodium nitrate and urea) and organic nitrogen sources (yeast extract, beef extract, corn steep liquor, and tryptone) at the same concentration. Beef extract was found to be the best nitrogen source resulting in the production of 5.2 gL$^{-1}$ of butanol (FIG. 6). Optimization of concentration showed that 5.0% w/v of beef extract is optimum for butanol production (7.8 gL$^1$) (FIG. 7).

To assess the effect of metal ions, the carbonate/sulphate/chloride salts of different metal ions (Na$^+$, Mg$^{++}$, Ca$^{++}$, Zn$^{++}$, K$^+$ Mn$^{++}$) at 0.5% concentration were separately added in the medium. A significant increase in butanol production (11.1 gL$^{-1}$) was achieved when the medium optimized so far was supplemented with Na$_2$CO$_3$ at 0.5%. Metal ion like Cu did not support any amount of butanol production (FIG. 8).

Among the various salts of sodium investigated including chloride, carbonate, sulphate and phosphate, carbonate was most effective for the production resulting in 11.2 gL$^{-1}$ of butanol (Table 2). Further, upon optimizing the concentration of Na$_2$CO$_3$, it was observed that 0.5% w/v is optimal for butanol production (11.0 gL$^{-1}$) (FIG. 9).

TABLE 2

Effect of different salts of the selected metal ion on butanol production

| Mineral Salts | Butanol, gL$^{-1}$ |
|---|---|
| Na$_2$CO$_3$ | 11.2 |
| Na$_2$SO$_4$ | 9.1 |
| NaCl | 9.7 |
| NaNO$_3$ | 10.2 |
| Na$_2$HPO$_4$ | 9.0 |
| NaHCO$_3$ | 11.1 |

Effect of inoculum size on butanol production was investigated. The optimized medium was inoculated with different inoculum size (1-10%). Inoculum at 1% was found to yield maximum butanol (14.5 gL$^{-1}$) (FIG. 10). However, with increase in the inoculum density beyond 2%, the production of butanol declined

Example 4

Determination of Butanol Tolerance

The butanol tolerance level of the strain used in the present investigation was evaluated. The strain was inoculated in 50 ml of the optimized AnS medium containing different concentrations of butanol (0.5%, 1.0%, 1.3% 1.5%, 1.8%, 2.0%, 2.5%). Bottles were incubated for 96 h at 37° C. under static conditions with gentle intermittent manual shaking. The strain was found to tolerate upto 2.5% butanol in the medium.

Example 5

Verification of the Process in 300 ml Medium

Butanol production in the optimized medium was validated in 500 ml anaerobic bottles containing 300 ml of the optimized medium. 1% of the inoculum was aseptically added with the help of syringe into the bottles and incubated at 37° C. for 96 h. A maximum of 20 gL-1 of butanol was produced.

Example 6

Scale Up of the Bio-butanol at 5 L Scale

The butanol production in optimized medium using *Clostridium beijerinckii* ATCC 10132 was scaled up to 5 L level in a 10 L fermentor (Bioflow IV, NBS, USA). The optimized AnS medium was sterilized in situ at 110° C. for 15 min. The medium was inoculated with 2% of the seed inoculum (OD$_{660\ nm}$≈0.6) and fermentation was carried out at 37±1° C. for 84 h. The impeller speed was initially adjusted to 100 rpm and compressed sterile N2 was initially flushed for 30 min to create anaerobic environment and was subsequently sparged intermittently into the fermentor at rate of 0.5 vvm. Samples were harvested periodically at an interval of 12 h and analyzed for butanol production using HPLC and GC. The fermentation parameters such as temperature, N$_2$ supply and agitation rate were continuously monitored and regulated.

The butanol production started at 24 h in the fermentor and a maximum of 20.3 gL$^{-1}$ of butanol was produced in 48 h. Thereafter, there was no significant increase in the production of butanol (FIG. 11 & Table 3) indicating a significant reduction in the production time of butanol at higher scale.

TABLE 3

Fermentation profile at 5 L scale

| Incubation period (h) | Butanol Production (gL$^{-1}$) |
|---|---|
| 12 | — |
| 24 | 5.9 |
| 36 | 14.6 |
| 48 | 20.3 |
| 60 | 21.2 |
| 72 | 19.4 |
| 84 | 19.1 |

Example 7

Study of the Various Biomass for Biobutanol Production

The results obtained using various biomass is listed in Table 4.

1. Pretreatment of Jatropha seed with fungal culture *Pleurotus ostreatus*

Finely ground jatropha seeds, (100 g, approx. mesh size 50 mm) was suspended in 50 ml of basal salt medium (0.5% glucose, 0.1% $KH_2PO_4$, 0.05% $MgSO_4.7H_2O$, 0.05% KCl, 0.05% yeast extract). To this 50 ml each of stock solution I and stock solution II were added (Stock solution I: 0.02% $FeSO_4.7H_2O$ and Stock solution II: 0.016% $Mn(CH_3COO)_2.4H_2O$, 0.004% $Zn(NO_3)_2.4H_2O$, 0.1% $Ca(NO_3)_2.4H_2O$, 0.006% $CuSO_4.5H_2O$). The entire mixture was autoclaved at 121° C. for 30 min and inoculated with 5-6 small malt extract (2%) agar blocks (1cm x 1cm) of two week old *Pleurotus ostreatus* (grown at 25° C.). The flask was incubated at 23° C. for 30 days. After incubation, 500 ml of 50 mM citrate buffer (pH 5.0) was added and the contents were mixed thoroughly by shaking on the rotary shaker (200 rpm) for 2 h. The contents of the flask was squeezed using muslin cloth and the solid biomass was used as a supplement at different concentrations (1, 3, 5, and 10%) in 50 ml Anaerobic Sugar (AnS) Medium having 0.5% calcium carbonate contained in 125 ml of the sealed anaerobic bottles. A maximum yield of 8.4 g/l of butanol was obtained after 48 h using 3% of the fungal pretreated Jatropha seed cake.

In addition to this, when 1% soybean meal was added in AnS medium supplemented with 0.5% calcium carbonate and 4% of Beef extract a maximum yield of 10.5 g/L of butanol after 96 h.

2. Banana Stem and Jatropha Seed Pretreated with Sodium Hydroxide Digestion Method
(a) The banana stem was cut into small pieces and 100 g of these banana stem pieces were kept in 500 ml of 0.5M NaOH for 24 h with intermittent gentle shaking. After 24 h, these pieces were washed with running tap water to remove the alkali and were added to the AnS medium having 0.5% of $CaCO_3$ at different concentrations for studying their effect on the production of butanol. The highest production of butanol 8.1 g/L was achieved in AnS medium containing 1% of the predigested banana stem.
(b) The jatropha seeds were finely ground and were put into 500 ml of 0.5M NaOH for 24 h at room temperature. After 24 h, these pieces were washed with running tap water to remove sodium hydroxide. The different concentrations of pretreated jatropha seed cake were added to ANS media (containing 0.5% calcium carbonate). The highest production of butanol 5.0 g/L when 1% of the predigested jatropha seed was added to the AnS medium having 0.5% calcium carbonate.

3. Microwave Digestion for Banana Stem and Jatropha Seeds
(a) The banana stem was cut into the small pieces and partially digested in microwave oven for 10 min. The digested banana stem was ground in a mixer and finely ground banana was again digested in a microwave for 5 min. Sugar was analyzed by DNS method. A maximum yield of 6.9 g/l of butanol was obtained after 84 h when 2% microwave treated banana stem was added to AnS medium having 0.5% calcium carbonate.
(b) The finely ground jatropha seed (20 g) was added to 500 ml distilled water and cooked for 10 min in microwave oven. Microwave treated jatropha seeds were cooled down and again treated for 10 min in microwave oven. Sugar was analyzed by DNS method. The results showed that a maximum of 7.0 g/l of butanol was obtained after 84 h using 1% microwave treated jatropha seed cake in the AnS medium supplemented with 0.5% calcium carbonate and 0.5 ml glycerol.

4. Banana Stem and Jatropha Seed Pretreated with 0.1N Sulphuric Acid
(a) The banana stem was cut into small pieces. Approximately, 100 g of these banana stem pieces were kept in 500 ml of 0.1N sulphuric acid for 24 h. These pieces were then washed with running tap water and were dried completely. The different concentration of this pretreated banana stem was then added to ANS media containing 0.5% calcium carbonate. The results showed that a maximum yield of 5.0 g/l of butanol was obtained after 84 h when 1% acid treated banana stem was added to AnS medium containing 0.5% calcium carbonate.
(b) The jatropha seed cake was ground. Approx. 50 g of the ground jatropha seeds were treated with 500 ml of 0.1N sulphuric acid for 24 hours. After 24 h, these pieces were washed with running tap water to remove sulphuric acid. The predigested jatropha seed cake was dried completely. This pretreated jatropha seed cake was added to ANS media (having 0.5% calcium carbonate) at different concentrations. A yield of 4.0 g/l of butanol was obtained after 84 h using 1% acid pretreated jatropha seed cake.

TABLE 4

Butanol production using biomass

| Biomass | Pre-treatment | Butanol, g/L |
|---|---|---|
| Jatropha seed cake | Fungal treatment with *Pleurotus ostreatus* | 8.4 |
| | 0.5 M NaOH | 5.0 |
| | 0.1 N Sulphuric acid | 4.0 |
| | Microwave digestion | 7.0 |
| Banana Stem | 0.5 M NaOH | 8.1 |
| | 0.1 N Sulphuric acid | 5.0 |
| | Microwave digestion | 6.9 |

Example 8

Solvent tolerance by *Clostridium beijerinckii* ATCC 10132

The butanol tolerance of *Clostridium beijerinckii* ATCC 10132 was studied by subjecting the bacteria to various concentrations of butanol in the growth medium ranging from 1.5% to 3.5%. The tolerance was tested in both, the un-optimized AnS medium and optimized AnS medium. The bottles were inoculated with *Clostridium beijerinckii* ATCC 10132 After inoculation, the medium was incubated at 37° C. for 144 h and the OD at 600 nm was monitored at a regular interval of 12 h. The results clearly indicate that the wild type *Clostridium beijerinckii* ATCC 10132 can tolerate up to 3.0% butanol under un-optimized conditions (FIG. 12 and 3.5% butanol under optimized conditions (FIG. 13).

Example 9

Mechanism of Solvent Tolerance in *Clostridium beijerinckii* ATCC 10132

The mechanism of solvent tolerance in *Clostridium beijerinckii* ATCC 10132 was evaluated by screening for overexpression of the heat shock protein GroEL. The butanol tolerant strain *Clostridium beijerinckii* ATCC 10132, was grown in 125 ml sealed anaerobic vial containing 50 ml of Anaerobic Sugar (AnS) medium with 2.3% butanol while the unadapted strain of *Clostridium beijerinckii* ATCC 10132 was grown AnS medium devoid of butanol. The bottles were incubated for 24 h at 37° C. under static conditions.

The cells were screened for overexpression of GroEL by western blotting. After the desired incubation period, 1.0 ml of the culture from each vial was withdrawn with the help of the sterilized disposable syringe and was centrifuged at 10,00 rpm at 4° C. for 20 min. The pellet was collected and dispensed in 100 μl of 0.1 M Tris buffer (pH 8.0). The pellet was sonicated and centrifuged for 1 min at 8500 rpm at 4° C. The supernatant was collected as the crude extract. For electrophoresis of proteins, crude extract of butanol tolerant strain and non-tolerant strain were run on sodium dodecyl sulfate-polyacrylamide gel (SDS-PAGE). The protein concentration in the extract was normalized in the extract.

Western Blot Analysis:

After electrophoresis, proteins were transferred to 0.2-μm Immun-Blot polyvinylidene difluoride membranes (Bio-Rad). The membranes were blocked with 5% skimmed milk in Tris-buffered saline plus Tween 20 (TBST) for 12-16 h before hybridization.

The blocked membrane was incubated for 1 hr with anti-GroEL antibody produced in rabbit (Sigma), at dilutions of 1:10,000. After incubation the membrane was washed thrice with TBST buffer for 5 min each. Monoclonal anti rabbit Immunoglobulins—Alkaline Phosphatase, antibody produced in mouse at dilution of 1:10,000 were used as a secondary antibody (Sigma). The membrane was incubated with the secondary antibody for 1 h. All antibody dilutions were prepared in TBST buffer. The membrane was washed with TBST buffer thrice for 5 min each. The membrane was developed with 5 ml of BCIP-NBT Solution (Sigma). The solvent-tolerant strain of *Clostridium beijerinckii* ATCC 10132 shows the presence of a prominent band of GroEL (FIG. 14, Lane 2) whereas in the un-adapted strain, the band is hardly visible (FIG. 14, Lane 1).

Example 10

Purification of Butanol by Fractional Distillation

For purification of butanol from the fermentation broth, the broth was centrifuged for separation of cells. The supernatant was subjected to fractional distillation. The distillate fraction obtained at a vapour temperature of 96° C. was collected and the fractions were analyzed for the butanol content by GC on a Agilent Gas chromatograph equipped with 30m×0.53 mm capillary column DB Wax 624 (J & W Scientific, USA) and a flame ionization detector. $N_2$ was used as the carrier gas The spilt ratio was set at 10:1. The detector temperature was 300° C. One microliter of the sample was injected (injector temperature 250° C.) in to the system for analysis. The recovery by fractional distillation was 47% with a purity of 91% (Table 1).

TABLE 5

Recovery of Butanol

| Sample | Volume | Butanol conc (g/L) | Total Butanol | % Recovery |
|---|---|---|---|---|
| Initial broth | 200 ml | 15.0 g/L | 3.0 g | |
| Fraction | 2.4 ml | 612 g/L | 1.4 g | 47 |

Example 11

General Parameters for HPLC-Based Determination (a) Evaluation of different columns, mobile phases and RT Three different columns, mobile phases were tried to estimate butanol on the HPLC (Shimadzu RID-10A monitor, LC-10AT pump, LTO-10AS column oven). These include:

| | |
|---|---|
| (i) Column | Rezex ROA, 300 mm × 7.8 m (Phenomenex, USA) |
| Detector | Refractive Index |
| Oven temperature | 37° C. |
| Mobile phase | MilliQ water |
| Flow rate | 0.6 ml/minute. |
| Retention time | 42.0 min |
| (ii) Column | Aminex HPX -87H (Biorad) |
| Detector | Refractive Index |
| Oven temperature | 37° C. |
| Mobile phase | 0.5 mM $H_2SO_4$ |
| Flow rate | 0.6 ml/minute. |
| Retention time | 32.0 min |
| (iii) Column | Hamilton PRP-X 300 (Hamilton) |
| Detector | Refractive Index |
| Oven temperature | 37° C. |
| Mobile phase | Acetonitrile: 0.5 mM $H_2SO_4$ (1:9) |
| Flow rate | 1.5 ml/minute. |
| Retention time | 7.3 min |

On the first two columns i.e. Rezex Organic and Aminex HPX column, the retention time for the estimation of butanol was 42 and 32 min respectively. However, on the Hamilton PRP300X column, butanol could be eluted in as little as 7.3 min.

(b) Evaluation of the Method at Different Sampling Times of the Fermentation to Follow the Rate of Reaction.

The samples were harvested at different incubation periods upto 96 h and were analyzed for the butanol concentration using PRP 300X column. The butanol concentration gradually increase until it reached a maximum at 84 h. Thereafter, the concentration of butanol remains almost constant.

Example 12

Standardized Conditions for Analysis

The columns used in the present invention is Hamilton PRP 300×

The mobile phase is Acetonitrile: 0.5 mM $H_2SO_4$ (1:9)

The detection device involves Refractive Index (RI) at a flow rate of 1.5 ml/min at 37° C.

The Sample Preparation:

The samples were withdrawn from the sealed vials using sterile disposable syringes. These samples were then centrifuged at 10,000 rpm for 10 minutes and supernatant was filtered through a 0.45μ filter prior to analysis.

The process of sampling of the fermentation culture medium involves harvesting the broth after the desired incubation period from the sealed anaerobic bottles using sterile disposable syringes. The broth is then centrifuged at 8000×g in a Eppendorf centrifuge for 10 min. The supernatant is then taken out and filtered through 0.45µ filter and 20 µl of this filtered supernatant sample is injected in the PRP 300X column (Hamilton).

The analysis: The sample (20 µl) was injected into the column using a Hamilton syringe. The retention time of butanol was recorded to be 7.3 min. The concentration of butanol was calculated by running the standard butanol (Sigma) in the range of 0.5-50 g/L as evident from FIGS. 15 and 16. Chromatograms shown in these figures clearly indicate that standard n-butanol elutes at a retention time of 7.3 min(FIG. 15). The sample also showed a peak at 7.3 min indicating the presence of n-butanol (FIG. 16).

REFERENCES

Agarwal, L., Isar, J., Saxena, R. K. (2005). Rapid screening procedures for identification of succinic acid producers. *J Biochem Biophys Methods.* 63 (1): 24-32.

Biebl, H. (1999). Comparative investigations of growth and solvent formation in 'Clostridium saccharoperbutylacetonicum' DSM 2152 and *Clostridium acetobutylicum* DSM 792. *J Ind. Microbiol. Biotechnol* 22: 115-120.

Ehrlich, G. G., Georlitz, D. F., Bourell, J. H., Eisen, G. V. and Godsy, E. M. (1981). Liquid Chromatographic Procedures for fermentation products analysis in identification of anaerobic bacteria. *Appl. Environ. Microbiol.* 42(5): 878-885.

Evan, P. J., and Wang, H. Y. (1988). Enhancement of butanol formation by *Clostridium acetobutylicum* in the presence of decanol-olely alcohol mixed extractants. *Appl. Environ. Microbiol.* 54: 1662-1667.

Ezeji, T. C., Qureshi, N., Blsachek, H. P. (2007). Bioproduction of butanol from biomass: from genes to bioreactors. *Curr. Opn Biotechnol.* 18: 220-227.

Fouad M, Abou-Zeid A A, Yassein M. (1976). The fermentative production of acetone-butanol by *Clostridium acetobutylicum. Acta Biol Acad Sci Hung.* 27 (2-3): 107-17.

Herrera, S. (2004). Industrial biotechnology—a chance at redemption. *Nature Biotechnol.* 22 (6): 671-678.

Isar, J., Agarwal, L., Saran, S., Gupta, P. and Saxena, R. K. (2006). Effect of process parameters on succinic acid production in *Escherichia coli* W3110 and enzymes involved in the reductive tricarboxylic acid cycle. *Can. J. Microbiol.* 52(9): 893-902.

Jesse, T. W., Ezeji, T. C., Qureshi, N. and Blaschek, H. P. (2002). Production of butanol from starch based waste packing peanuts and agricultural waste. *J. Ind. Microbial. Biotechnol.* 29: 117-123.

Jones, D. T. and Woods, D. R. (1986). Acetone butanol fermentation Revisited. *Microbiol. Rev.* 50 (4): 484-524.

Lee, P. C., Lee, W. G., Lee, S. Y., Chang, H. N. (1999). Effects of medium components on the growth of *Anaerobiospirillum succiniciproducens* and succinic acid production. *Process Biochem.* 35:49-55.

Lee, P. C., Lee, W. G., Kwon, S., Lee, S. Y., and Chang, H. N. (2000). Batch and continuous cultivation of *Anaerobiospirillum succiniproducens* for the production of succinic acid from whey. *Appl. Microbiol. Biotechnol.* 54: 23-27.

Lin, Y. L. and Blaschek, H. P. (1983). Butanol production by a butanol—tolerant train of *Clostridium acetobutylicum* in extruded corn broth. *Appl. Environ Microbiol.* 45: 966-973.

Long, S., Long, D. T., and Woods, D. R. (1984). Initiation of solvent production, clostridial stage and endospore formation in *Clostridium acetobutylicum* P262. Appl. *Microbiol. Biotechnol.* 20: 256-261.

McCutchan, W. N., and Hickey, R. J. (1954). The butanol—acetone fermentation. Ind. Ferment. 1: 347-388.

Moon, S. H. and Parulekar, S. J. (1991). A parametric study of protease production in batch and fed-batch cultures of *Bacillus firmus. Biotechnol. Bioeng.* 37, 467-483.

Moreira, A. R., Ulmer, D. C., Linden, J. C. (1981). Butanol toxicity in the butylic fermentation. *Biotechnol Bioeng. Symp.* 11: 567-579.

Mutschlechner O, Swoboda H, Gapes J R (2000). Continuous two-stage ABE-fermentation using *Clostridium beijerinckii* NRLL B592 operating with a growth rate in the first stage vessel close to its maximal value. *J. Mol. Microbiol. Biotechnol.* 2(1):101-5.

Nghiem, N. P., Davidson, B. H., Suttle, B. E., Richardson, G. R. (1997). Production of succinic acid by *Anaerobiospirillum succiniciproducens. Appl Biochem Biotechnol* 63-65: 565-576.

Parekh, M., Formanek and Blaschek, H. P. (1998). Development of a cost effective glucose—corn steep medium for production of butanol by *Clostridium beijerinckii. J. Ind. Microbiol. Biotechnol.* 21: 187-191.

Qureshi, N. and Blaschek, H. P. (1999). Production of acetone butanol ethanol (ABE) by a hyper-producing mutant strain of *Clostridium beijerinkii BA*101 and recovery by pervaporation. *Biotechnol. Prog.* 15: 594-602.

Qureshi, N., Lolas, A., Blaschek, H. P. (2001). Soy molasses as fermentation substrate for production of butanol using *Clostridium beijerinkii* BA101. *J. Ind. Microbiol. Biotechnol.* 26: 290-295.

Robson, P. M., and Jones, D. T. (1982). Production of acetone—butanol by industrial fermentation, In O. Chaude and Durand, G (ed.), *Industrielle et Biotechnologie.* p 169-214.

Samuelov N S, Lamed R, Lowe S, Zeikus J G. (1991). Influence of $CO_2$ $HCO_3$+ levels and pH on growth, succinate production and enzyme activities of *Anaerobiospirillum succiniciproducens. Appl. Environ. Microbiol.* 57:3013-9.

Strobel, H. J., Russel, J. B. (1991). Role of sodium in the growth of a ruminal selenomonad. *Appl Environ Microbiol.* 57: 1663-1669.

Zeikus, J. G. (1980). Chemical and fuel production by anaerobic bacteria. *Ann Rev Microbiol* 34: 423-464.

Thus, while we have described fundamental novel features of the invention, it will be understood that various omissions and substitutions and changes in the form and details may be possible without departing from the spirit of the invention. For example, it is expressly intended that all combinations of those elements and/or method steps, which perform substantially the same function in substantially the same way to achieve the same results, be within the scope of the invention.

The invention claimed is:

1. A continuous process for production of butanol and acetone comprising: establishing and maintaining a culture in a fermentor, said culture comprising *Clostridium beijerinckii* ATCC 10132 and a nutrient medium comprising glucose, malt extract, and beef extract, wherein the concentration of the glucose in the nutrient medium is about 2%, the concentration of the malt extract in the nutrient medium is about 5%, and the concentration of the beef extract is about 5%; maintaining the concentrations of glucose, malt extract, beef extract and *Clostridium beijerinckii* ATCC 10132 in the fermentor at levels sufficient to maintain a continuous process; wherein the process is carried out without removing acetone or butanol from the fermenter; wherein the process is carried out at a temperature between 33° C. and 39°, at a pH in the range of 5.0 to 7.0 and with an inoculum density in the range of 1 to 2%; and wherein the process results in a yield of at least 20 g/L of butanol and the *Clostridium beijerinckii* ATCC 10132 tolerating a butanol concentration of about 2.5% in the nutrient medium.

2. The process of claim 1, wherein the temperature is 37° C.

3. The process of claim 1, wherein the nutrient medium is supplemented with 0.6% $Na_2CO_3$.

4. The process of claim 1, wherein the nutrient medium is supplemented with 0.5% of calcium carbonate.

* * * * *